United States Patent [19]
Willey

[11] Patent Number: 5,643,765
[45] Date of Patent: Jul. 1, 1997

[54] METHOD FOR QUANTITATIVE MEASUREMENT OF GENE EXPRESSION USING MULTIPLEX COMPETITIVE REVERSE TRANSCRIPTASE-POLYMERASE CHAIN REACTION

[75] Inventor: James C. Willey, Rochester, N.Y.

[73] Assignee: University of Rochester, Rochester, N.Y.

[21] Appl. No.: 43,390

[22] Filed: Apr. 6, 1993

[51] Int. Cl.$^6$ .............................. C12P 19/34; C12Q 1/68
[52] U.S. Cl. .............................. 435/91.2; 435/6; 935/77; 935/78
[58] Field of Search .............................. 435/91.2, 91.51, 435/6; 536/24.33

[56] References Cited

U.S. PATENT DOCUMENTS

| | | | |
|---|---|---|---|
| 4,683,195 | 7/1987 | Mullis et al. | 435/91.2 |
| 4,683,202 | 7/1987 | Mullis et al. | 435/91.2 |
| 4,965,188 | 10/1990 | Mullis et al. | 435/91.2 |

OTHER PUBLICATIONS

Araki et al. (Mar. 1993) J. Bone Min. Res. 8(3):313–322.
Apostolakos et al. (May 1, 1992) Clinical Research Abstract. Presentation.
Quantitation of Changes in the Expression of Multiple Genes by Simultaneous Polymerase Chain Reaction, Dukas et al., Analytical Biochemistry 215, 66–72 (1993).
Gilliland, G., et al., *Proc. Natl. Acad. Sci.* 87: 2725–2729 (1990).
Horikoshi, T., et al., *Cancer Res.* 52:108–116 (1992).
Noonan, K.E., et al., *Proc. Natl. Acad. Sci.* 87:7160–7164 (1990).
Murphy, L.D., et al., *Biochemistry* 29:10351–10356 (1990).
Carre, P.C., et al., *J. Clin. Invest.* 88:1802–1810 (1991).
Chelly, J., et al., *Eur. J. Biochem* 187:691–698 (1990).
Abbs, S., et al., *J. Med. Genet.* 29:191–196 (1992).
Feldman, A.M. et al., *Circulation* 83:1866–1872 (1991).
Siebert, P.D., et al., *Nature* 359:557–558 (1992).
Siebert, P.D., et al., *BioTechnologies* 14:244–249 (1993).
Clontech Brochure, 1993, Reverse Transcriptase–PCR (RT–PCR).
Celi et al, *Nucleic Acids Res.*, 21, 1047 (1993).
Devereux et al. *N A R* 12 387 (1984).
Barbu et al., *N A R* 17 7115 (1989).
Willey et al, *Cancer Res.* 51:5370–5377 (1990).
Chomczynski and Sacchi (*Analytical Biochemistry* 162:156–159 (1987).
Chada et al., *Genomics* 6:268–271 (1990).
Tso et al., *Nucleic Acids Res.* 13:2485–2502 (1985).
Higuchi et al., *Nucleic Acids Res.* 16:7351–7367 (1988).
Becker-Andre et al., *Nucleic Acids Res.* 17:9437–9446 (1989).
Jaiswal, et al., *Science* 228:80–83 (1985).
Pannetier et al., *Nucleic Acids Res.* 21:577–583 (1993).
Apostolakos et al., *Anal. Biochem.* 213:277–284 (1993).
Overby et al., *Mol. Pharmacology* 41:1039–1046 (1992).

*Primary Examiner*—W. Gary Jones
*Assistant Examiner*—Lisa Arthur
*Attorney, Agent, or Firm*—Emch, Schaffer, Schaub & Porcello

[57] ABSTRACT

A method for quantitative measurement of gene expression through multiplex competitive reverse transcriptase polymerase chain reaction amplification has been established which comprises isolating cellular mRNA of a target gene and a housekeeping gene which are then reverse transcribed and specifically amplified in the presence of competitive templates such that a ratio of target to housekeeping gene is obtained and used to assess the amount of gene expression. This method is useful for analysis of the small specimens (cells and tissues) available from human subjects and will allow improved understanding of mechanisms of disease.

22 Claims, 4 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: Homo Sapiens
        ( H ) CELL LINE: HL-60

( x ) PUBLICATION INFORMATION:
        ( A ) AUTHORS: Chada, S.
                Le Beau, M. M.
                Casey, L.
                Newberger, P. E.
        ( C ) JOURNAL: Genomics
        ( D ) VOLUME: 6
        ( F ) PAGES: 268-271
        ( G ) DATE: September-1990

( x i ) SEQUENCE DESCRIPTION: SEQ ID NO:1:

```
GGGGCCTGGT GGTGCTCGGC T                                    21
```

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: Homo Sapiens
        ( H ) CELL LINE: HL-60

( x ) PUBLICATION INFORMATION:
        ( A ) AUTHORS: Apostolakos, Michael J.
                Schuermann, Wolfgang H.T.
                Frampton, Mark W.
                Utell, Mark J.
                Willey, James C.
        ( B ) TITLE: Measurement of Gene Expression by Multiplex Competitive Polymerase Chain Reaction
( C ) JOURNAL: Anal. Biochem.
( D ) VOLUME: 213
( F ) PAGES: 277-284
( G ) DATE: September-1993
( K ) RELEVANT RESIDUES IN SEQ ID NO:2: FROM 241 TO 261

( x i ) SEQUENCE DESCRIPTION: SEQ ID NO:2:

CAATGGTCTG GAAGCGGCGG C                                                     2 1

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: Homo Sapiens
        ( D ) DEVELOPMENTAL STAGE: Adult
        ( H ) CELL LINE: HL-60

( x ) PUBLICATION INFORMATION:
        ( A ) AUTHORS: Chada, S.
                Le Beau, M. M.
                Casey, L.
                Newberger, P. E.
        ( C ) JOURNAL: Genomics
        ( D ) VOLUME: 6
        ( F ) PAGES: 268-271
        ( G ) DATE: 1990

( x i ) SEQUENCE DESCRIPTION: SEQ ID NO:3:

ATTCTGATTT CCCTCAAGTA CGTCCGGCCT                                             3 0

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i v ) ANTI-SENSE: NO     ( v ) FRAGMENT TYPE: internal     ( v i ) ORIGINAL SOURCE:
        ( A ) ORGANISM: Homo Sapiens
        ( D ) DEVELOPMENTAL STAGE: Adult
        ( H ) CELL LINE: HL-60

( x ) PUBLICATION INFORMATION:
        ( A ) AUTHORS: Chada, S.
                Le Beau, M. M.
                Casey, L.
                Newberger, P. E.
        ( C ) JOURNAL: Genomics
        ( D ) VOLUME: 6
        ( F ) PAGES: 268-271
        ( G ) DATE: 1990

( x i ) SEQUENCE DESCRIPTION: SEQ ID NO:4:

TAAGACTAAA GGGAGTTCAT GCAGGCCGGA 30

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: double
        (D) TOPOLOGY: linear     (ii) MOLECULE TYPE: cDNA     (iii) HYPOTHETICAL: NO     (iv) ANTI-SENSE: NO     (v) FRAGMENT TYPE: internal     (vi) ORIGINAL SOURCE:
        (A) ORGANISM: Homo Sapiens
        (D) DEVELOPMENTAL STAGE: Adult
        (F) TISSUE TYPE: Liver
        (G) CELL TYPE: Hepatocellular     (x) PUBLICATION INFORMATION:
        (A) AUTHORS: Tso, J. Y.
            Sun, X.
            Kao, T.
            Reese, K. S.
            Wu, R.
        (C) JOURNAL: Nucleic Acids Research
        (D) VOLUME: 13
        (F) PAGES: 2485-2502
        (G) DATE: 1985

(xi) SEQUENCE DESCRIPTION: SEQ ID NO:5:

GGTCGGGAGT CAACGGATTT GGTCG 25

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: double
        (D) TOPOLOGY: linear     (ii) MOLECULE TYPE: cDNA     (iii) HYPOTHETICAL: NO     (iv) ANTI-SENSE: NO     (v) FRAGMENT TYPE: internal     (vi) ORIGINAL SOURCE:
        (A) ORGANISM: Homo Sapiens
        (D) DEVELOPMENTAL STAGE: Adult
        (F) TISSUE TYPE: Liver
        (G) CELL TYPE: Hepatocellular     (x) PUBLICATION INFORMATION:
        (A) AUTHORS: Tso, J. Y.
            Sun, X.
            Kao, T.
            Reece, K. S.
            Wu, R.
        (C) JOURNAL: Nucleic Acids Research
        (D) VOLUME: 13
        (F) PAGES: 2485-2502
        (G) DATE: 1985

(xi) SEQUENCE DESCRIPTION: SEQ ID NO:6:

CCTCCGACGC CTGCTTCACC AC 22

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear    ( i i ) MOLECULE TYPE: cDNA   ( i i i ) HYPOTHETICAL: NO    ( i v ) ANTI-SENSE: NO     ( v ) FRAGMENT TYPE: internal    ( v i ) ORIGINAL SOURCE:
        ( A ) ORGANISM: Homo Sapiens
        ( D ) DEVELOPMENTAL STAGE: Adult
        ( F ) TISSUE TYPE: Liver
        ( G ) CELL TYPE: Hepatocellular     ( x ) PUBLICATION INFORMATION:
        ( A ) AUTHORS: Tso, J. Y.
                Sun, X.
                Kao, T.
                Reece, K. S.
                Wu, R.
        ( C ) JOURNAL: Nucleic Acids Research
        ( D ) VOLUME: 13
        ( F ) PAGES: 2485-2502
        ( G ) DATE: 1985

( x i ) SEQUENCE DESCRIPTION: SEQ ID NO:7:

TGATCAATGG AATTCCCATC ACCA  24

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear    ( i i ) MOLECULE TYPE: cDNA   ( i i i ) HYPOTHETICAL: NO    ( i v ) ANTI-SENSE: NO     ( v ) FRAGMENT TYPE: internal    ( v i ) ORIGINAL SOURCE:
        ( A ) ORGANISM: Homo Sapiens
        ( D ) DEVELOPMENTAL STAGE: Adult
        ( F ) TISSUE TYPE: Liver
        ( G ) CELL TYPE: Hepatocellular     ( x ) PUBLICATION INFORMATION:
        ( A ) AUTHORS: Tso, J. Y.
                Sun, X.
                Kao, T.
                Reece, K. S.
                Wu, R.
        ( C ) JOURNAL: Nucleic Acids Research
        ( D ) VOLUME: 13
        ( F ) PAGES: 2485-2502
        ( G ) DATE: 1985

( x i ) SEQUENCE DESCRIPTION: SEQ ID NO:8:

ACTAGTTACC TTAAGGGTAG TGGT  24

( 2 ) INFORMATION FOR SEQ ID NO:9:

( i ) SEQUENCE CHARACTERISTICS:
        ( A ) LENGTH: 20 base pairs (B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
(A) ORGANISM: Homo Sapiens
(D) DEVELOPMENTAL STAGE: Adult
(F) TISSUE TYPE: Liver
(G) CELL TYPE: Hepatocellular (x) PUBLICATION INFORMATION:
(A) AUTHORS: Tso, J. Y.
Sun, X.
Kao, T.
Reece, K. S.
Wu, R.
(C) JOURNAL: Nucleic Acids Research
(D) VOLUME: 13
(F) PAGES: 2485-2502
(G) DATE: 1985

(xi) SEQUENCE DESCRIPTION: SEQ ID NO:9:

CATGGCACCG TCAAGGCAAC 20

(2) INFORMATION FOR SEQ ID NO:10:

(i) SEQUENCE CHARACTERISTICS:
(A) LENGTH: 22 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
(A) ORGANISM: Homo Sapiens
(D) DEVELOPMENTAL STAGE: Adult
(F) TISSUE TYPE: Liver
(G) CELL TYPE: Hepatocellular (x) PUBLICATION INFORMATION:
(A) AUTHORS: Tso, J. Y.
Sun, X.
Kao, T.
Reece, K. S.
Wu, R.
(C) JOURNAL: Nucleic Acids Research
(D) VOLUME: 13
(F) PAGES: 2485-2502
(G) DATE: 1985

(xi) SEQUENCE DESCRIPTION: SEQ ID NO:10:

CCTCCGACGC CTGCTTCACC AC 22

(2) INFORMATION FOR SEQ ID NO:11:

(i) SEQUENCE CHARACTERISTICS:
(A) LENGTH: 26 base pairs
(B) TYPE: nucleic acid
(C) STRANDEDNESS: double
(D) TOPOLOGY: linear (i i) MOLECULE TYPE: cDNA (i i i) HYPOTHETICAL: NO (i v) ANTI-SENSE: NO (v) FRAGMENT TYPE: internal (v i) ORIGINAL SOURCE:
                (A) ORGANISM: Homo Sapiens
                (D) DEVELOPMENTAL STAGE: Adult
                (F) TISSUE TYPE: Liver (x i) SEQUENCE DESCRIPTION: SEQ ID NO:11:

CAGGGGGGAT CCAAAAGGGT CATCAT 26

(2) INFORMATION FOR SEQ ID NO:12:

(i) SEQUENCE CHARACTERISTICS:
                (A) LENGTH: 26 base pairs
                (B) TYPE: nucleic acid
                (C) STRANDEDNESS: double
                (D) TOPOLOGY: linear (i i) MOLECULE TYPE: cDNA (i i i) HYPOTHETICAL: NO (i v) ANTI-SENSE: NO (v) FRAGMENT TYPE: internal (v i) ORIGINAL SOURCE:
                (A) ORGANISM: Homo Sapiens
                (D) DEVELOPMENTAL STAGE: Adult
                (F) TISSUE TYPE: Liver (x) PUBLICATION INFORMATION:
                (A) AUTHORS: Tso, J. Y.
                        Sun, X.
                        Kao, T.
                        Reese, K. S.
                        Wu, R.
                (C) JOURNAL: Nucleic Acids Research
                (D) VOLUME: 13
                (F) PAGES: 2485-2502
                (G) DATE: 1985

(x i) SEQUENCE DESCRIPTION: SEQ ID NO:12:

GTCCCCCCTA GGTTTTCCCA GTAGTA 26

METHOD FOR QUANTITATIVE MEASUREMENT OF GENE EXPRESSION USING MULTIPLEX COMPETITIVE REVERSE TRANSCRIPTASE-POLYMERASE CHAIN REACTION

The present invention was made under research grant number ES02679 and ES01247 from the National Institute of Health; Grant No. RR00044 from the Division of Research Resources, Health Institute Contract 91-2, and International Lead Zinc Organization contract CH61, who may have certain rights thereto. The present invention relates generally to a method for measurement of cellular levels of RNA following reverse transcription and polymerase chain reaction amplification.

TECHNICAL BACKGROUND

Previously described methods allow amplification of PCR-amplified cDNA but do not satisfactorily allow quantification (Noonan et al, *Proc. Natl. Acad. Sci.* 87:7160–7164,1990). Another recently described method (Gilliland et al. *Proc. Natl. Acad. Sci.* 8 7:2725–2729, 1990) is an improvement in this regard, but still does not include a housekeeping gene internal standard and leaves intact the possibility of error due to variation in aliquoting of the RNA or cDNA sample from one tube to another.

The yield of product from PCR increases exponentially for an indefinite number of cycles. At some point and for uncertain reasons, the reaction becomes limited and PCR product increases at an unknown rate. Consequently, the yield of amplified product has been reported to vary by as much as 6-fold between identical samples run simultaneously. (Gilliland, G., et al., *Proc. Natl. Acad. Sci.* 87: 2725– 2729, 1990). Therefore, after a certain number of PCR cycles, the initial concentrations of target DNA cannot be accurately determined by extrapolation. In an attempt to make PCR quantitative, various investigators have analyzed samples amplified for a number of cycles known to provide exponential amplification (Horikoshi, T., et al., *Cancer Res.* 52:108–116 (1992); Noonan, K. E., et al., *Proc. Natl. Acad. Sci.* 87:7160–7164 (1990); Murphy, L. D., et al., *Biochemistry* 29:10351–10356 (1990); Carre, P. C., et al., *J. Clin. Invest.* 88:1802–1810 (1991); Chelly, J., et al., *Eur. J. Biochem* 187:691–698 (1990); Abbs, S., et al., *J. Med. Genet.* 29:191–196 (1992); Feldman, A. M. et al., *Circulation* 83:1866–1872 (1991). In general, this is early in the PCR when the PCR product is measurable by use of radiolabeled probes and autoradiography but not by spectrophotometry or densitometry of ethidium bromide stained gels. The use of radioactivity is inconvenient, expensive, and presents safety concerns. Also, the exponential phase must be defined for each set of experimental conditions, requiring additional cost in time and materials.

PCR in the presence of single base mutated competitive templates has been used as an alternative method to make PCR quantitative, Gilliland, supra; Becker-Andre, et al., *Nucleic Acids Res.* 17:9437–9446 (1989). A known amount of competitive template is co-amplified with an unknown amount of target sequence. The competitor is the same sequence (except for single base mutation) as the target, uses the same primers for amplification as the target cDNA, and amplifies with the same efficiency as the target cDNA. Therefore, the starting ratio of target/standard is preserved throughout the entire amplification process, even after the exponential phase is complete.

Competitive PCR is discussed in general in Siebert, P. D., et al., *Nature* 359:557–558 (1992); Siebert, P. D., et al., *BioTechniques* 14:244–249 (1993), and Clontech Brochure, 1993, Reverse Transcriptase-PCR (RT-PCR). All references disclosed herein are expressly incorporated by reference.

However, competitive PCR alone does not adequately control for variation in starting amounts of template. Degradation of samples and pipetting errors can lead to variation. This problem has been circumvented for Northern analysis by probing the same blot for both target gene and a "housekeeping" gene not expected to vary among tissue samples or in response to stimuli. The "housekeeping" gene acts as a denominator in determining the relative expression of a target gene. This constitutive control is just as important when attempting to quantitate or quantify gene expression using PCR. Methods have been described in various of the references cited above, whereby the target gene and the "housekeeping" gene are PCR-amplified in separate tubes. Under these conditions, intertube variation in amplification conditions and pipetting errors remain. Non-competitive multiplex PCR, where the target and "housekeeping" gene are amplified in the same tube, has also been described in Noonan, supra. This method is inconvenient because it requires the generation of standard curves to determine the exponential range of amplification for each target sequence. It also requires the use of radioactive probes.

SUMMARY OF THE INVENTION

Expression was measured by multiplex competitive PCR amplification of a) cDNA from the gene of interest and a "housekeeping" gene such as glyceraldehyde-3-phosphate dehydrogenase (GAPDH) and b) two internal standards consisting of either single base mutants of the gene of interest and the "housekeeping" gene cDNA that cause either a loss or gain of a restriction endonuclease recognition site or the sequences of the gene of interest and the "housekeeping" gene that have been shortened by recently described methods (Cell et al, *Nucleic Acids Research*, 21, 1047, 1993) while retaining sequences homologous to both primers used in PCR amplification. RNA extracted from cells or tissues was reverse transcribed. Serial dilutions of cDNA were PCR amplified in the presence of oligonucleotides homologous to the test gene and the "housekeeping" gene, and quantified amounts of mutated internal standards. The amplified DNA was restriction digested and electrophoresed on an agarose gel stained with ethidium bromide, separating native from mutated products. Densitometry was performed to quantify the bands. This technique to measure the relative expression of a gene to a "housekeeping" gene is precise and reproducible for studies done with the same master mixture and dilution of internal standards. Ratios of relative gene expression vary less than 25% from the mean. This technique will be useful to measure changes in gene expression when the amount of study sample is limited or the level of gene expression is low.

It is, therefore, the object of the present invention to provide an improved method for quantitative measurement of gene expression relative to a "housekeeping" gene in PCR-amplified cDNA.

It is a further object of the present invention to provide a method for quantitative PCR-based measurement of gene expression that is suitable as a commercial product.

These and other objects, features and many of the attendant advantages of the invention will be better understood upon a reading of the following detailed description when considered in connection with the accompanying drawings wherein.

DETAILED DESCRIPTION OF THE INVENTION

For many years, gene expression has been measured through quantification of RNA by Northern or dot blot analysis. These techniques require the amount of RNA obtainable from at least $10^5$ cells for each measurement. Often, a biopsy will provide only the number of cells necessary for a histological diagnosis and this is often far less than $10^5$ cells. Recently developed PCR techniques allow measurement of RNA levels in as few as 100 cells. However, techniques described thus far allow only qualitative, not quantitative measurement.

The present invention relates to a method using multiplex competitive reverse-transcriptase polymerase chain reaction amplification to simplify and improve quantitative measurement of gene expression. DNA extracted from samples is reverse transcribed and then subjected to PCR amplification in the presence of primers for both a "housekeeping" gene and the gene of interest.

The expression of genes is measured by comparing them to the level of a "housekeeping" gene. In the literature, there are three "housekeeping" genes that have been used as internal standards in Northern analyses of gene expression, including GAPDH, β-actin and 28S RNA (Devereux et al. NAR 12387, 1984; Barbu et al., NAR 177115, 1989). According to the present invention, synthesized oligonucleotides homologous to all sequences containing known restriction endonuclease recognition sites or one or two-basepair mismatches for all known restriction endonuclease sites that are present in GAPDH, β-actin and 28S RNA and 18S RNA can be utilized. The application of these restriction endonuclease recognition sites is to either routate the naturally occurring ones to non-recognition sites or to routate the mismatch sites to match sites, in either case creating mutant sequences suitable for internal standards. The particular sites in the "housekeeping gene" used for analysis of any particular other gene depends on the match and mismatch sites that are present in the other gene. The main determinant is the size of the DNA fragments that are generated from the "housekeeping gene" and the test gene. These fragments must separate well on gel electrophoresis.

Further, all oligonucleotides that contain sequences homologous to sequences in the genes for GAPDH, β-actin, or 28S RNA to be used in generating artificially shortened competitive templates according to the method described by Celi et al, 1993, can be used in the present inventive method of multiplex competitive reverse transcription-polymerase chain reaction.

To identify match and one or two base mismatch sequences for all known recognition sites, it is possible to use the Map program within the Genetics Computer Group software package (Devereux et al., 1984). The cDNA sequences are obtained for each gene, then each gene is evaluated for the presence of the match of one or two base pair mismatch sequences for every known restriction endonuclease. According to the present invention, it is possible to use every gene containing each of these recognition sequences or one or two base pair mismatches of these sequences.

Figure 3:
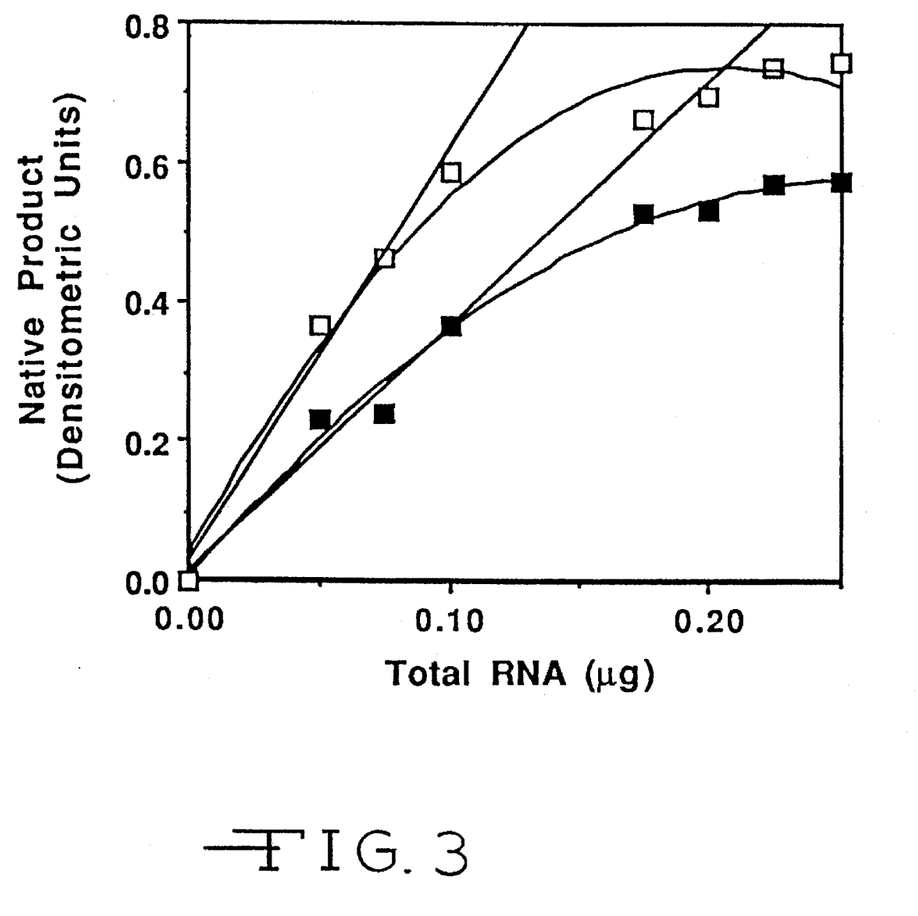
FIG. 3 is a graph showing the native product (□GSH-Px and ■GAPDH) vs. total RNA. With small amounts of starting RNA (first three squares for both GSH-Px) and GAPDH), the reactions are exponential throughout, however, with increasing amounts of RNA, the reaction becomes non-exponential at some point during amplification, resulting in less product formation than expected in a non-limited reaction. The straight lines represent the theoretical amounts of PCR product (either GSH-Px or GAPDH) which would have formed if amplification remained exponential throughout the amplification process.
Figure 4:
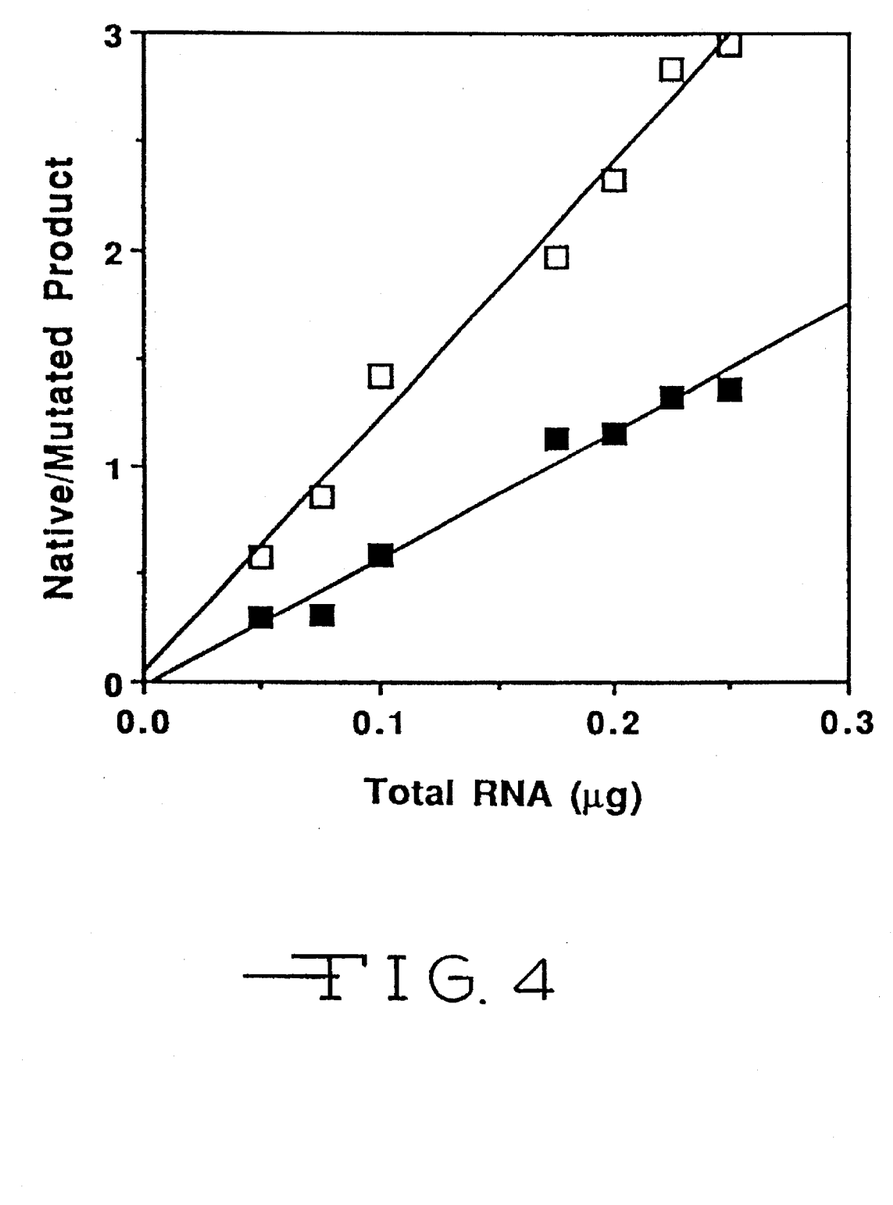
FIG. 4 is a graph showing Native/Mutated amplification products (□GSH-Px and ■GAPDH) vs. Total RNA. The relationship remains linear for both GSH-Px ($r^2$=0.982) and GAPDH ($r^2$=0.973) throughout the range of total RNA studied. This is consistent with the findings of Gilliland et al., *Proc. Natl. Acad. Sci.*, 87:2725–2729, 1990. This relationship attests to the quantitative nature of multiplex competitive PCR.

The present inventive multiplex competitive PCR (for any given master mixture and dilution of mutated standards) yields reproducible ratios of target gene/constitutive control gene. The quantitative results are illustrated by the linear relationship between the target gene/internal standard vs. total starting RNA for each of the genes as seen in FIG. 4 described below. Because the relationship between the amount of native product vs. total starting RNA did not remain linear with increasing amounts of RNA as seen in FIG. 3, described below, it is clear that the amplification is not exponential throughout. However, consistent target/"housekeeping" gene ratios are obtained with the use of a competitive template for each. This illustrates the utility of competitive template internal controls; it is not necessary to remain in the exponential phase of amplification to quantify relative amounts. The reproducibility of the ratio between samples in the same study allows for the use of fewer dilution tubes. Only one tube, in which all bands are quantifiable, is necessary for measurement of gene expression. This simplifies the procedure and permits the evaluation of many different samples at one time.

Several aspects of this PCR technique require attention. One aspect is the choice of restriction endonuclease recognition sites to separate mutated from native products. Another aspect is the ultimate PCR product lengths present after restriction endonuclease digestion. In certain embodiments, agarose gels are generally easier to use than polyacrylamide gels, but require greater DNA fragment size differences for adequate separation (approximately 50–100 base pair differences). The method of the present invention can be further simplified by the availability of the same recognition site for both the target and "housekeeping" gene. EcoRI sites are often appropriate, GAPDH competitive templates have been prepared that separate from native GAPDH on the basis of EcoRI or BamHI digestion. However, it is also possible to expect separation on the basis of EcoRI digestion that is compatible with a greater number of genes.

A large variation (up to 200-fold) in the GSH-Px/GAPDH gene expression ratio has been observed in studies performed on human papillomavirus-immortalized human bronchial epithelial cell line discussed in Willey et al., Cancer Research 51:5370–5377 (1991) BEP2D cDNA using different master mixtures and dilutions of mutated standards. Since samples that underwent reverse transcription separately gave similar results, the amount of variability introduced at this step is small. Any differences in reaction conditions will equally affect amplification of competitive template as well as native template and thus the ratio between the two will remain constant. Therefore, the variability likely results from differences in the amount of mutated standard in the reaction. The concentration of competitive template is so small (attomolar range) that any change in the number of molecules present in the reaction would introduce a large source of error.

The method of the present invention is precise in any given study as illustrated by the reproducibility between samples using the same master mixture with internal standards. Therefore, it is desirable that comparative samples be run simultaneously using the same master mixture with the same dilution of internal standards.

Multiplex competitive PCR improves and simplifies quantitation of gene expression. Gene expression can be quantitated in very small samples of tissue or cells without resorting to radiolabeling. As a result, it is less expensive and safer. The results are reproducible for studies using the same master mixture and dilutions of internal standards. The true utility of the quantitative PCR method of the present invention exists when study or sample material is quite limited. Other uses of this technique include evaluating gene expression from tissues obtained by endoscopic biopsy (brush or forceps), needle aspiration, and bone marrow biopsy.

METHODS

Purified deoxyribonucleotides obtained from Pharmacia (Piscataway, N.J.) were diluted to a stock solution of 10 mM. Recombinant *Thermus aquaticus* DNA polymerase (Taq polymerase), Avian myeloblastosis virus (AMV) reverse transcriptase, and ribonuclease inhibitor (RNasin) were obtained from Promega (Madison, Wis.). EcoRI enzyme was obtained for USB (Cleveland, Ohio). Primers were prepared on an Applied Biosystems model 391 PCR-Mate EPTM synthesizer. PCR was performed in a Perkins, Elmer, Cetus DNA Thermal Cycler 480. The other buffers and solutions used were from various sources and were molecular biology grade.

Studies were performed on a human papillomavirus-immortalized human bronchial epithelial cell line (BEP2D) (Willey et al, *Cancer Res.* 5 1:5370–5377, 1990).

The isolation of RNA was as follows: RNA was isolated based on the method described by Chomczynski and Sacchi (*Analytical Biochemistry* 162:156–159, 1987) Culture medium was removed from flasks containing the BEP2D cell line. Immediately GIT (4.0M guanidinium thiocyanate, 0.1M Tris Cl Ph=7.5, 1% beta-mercaptoethanol) buffer was placed on the cells (approximately 500 μL per 5–10 million BEP2D cells). Each 500 μL of GIT buffer containing the lysed cells was then transferred to a 1.5 mL microfuge tube. To each microfuge tube was added sequentially 50 μL of 2M Na acetate pH=4,500 NL of water saturated phenol and 100 mL of chloroform-isoamyl alcohol mixture (49:1). The tubes then were shaken thoroughly, placed on ice for 15 min, and microcentrifuged for 20 min at 14,000 RPM and 4° C. The aqueous phase of each tube was transferred to a fresh tube and the above extraction was repeated. Again, the aqueous phase of each tube was transferred to a fresh tube with isopropanol (500 μL), and placed at −70° C. for 15 min. The tubes were then microcentrifuged for 20 min at 14,000 RPM and 4° C. The RNA was washed twice with 70% ethanol and vacuum dried. RNA was taken up in 0.1% diethyl pyrocarbonate (DEPC) treated $H_2O$ and quantified by spectrophotometry (Gilford Instrument Spectrophotometer 260).

The reverse transcription was conducted as follows: the extracted RNA was placed in a sterile microfuge tube. For each 1 μg of RNA, 0.2 mg oligo dT was added. This was heated at 65° C. for 5 min and placed on ice for one min. To this was added 2 μL 1- mM dNTP's, 2 μL reverse transcriptase (RT) buffer (500 mM Tris, 400 mM KCl, and 80 mM Mg $Cl_2$), 0.5 μL RNasin, and 1 μL AMV reverse transcriptase (9.500 units/ml). This was incubated at 42° C. for one hour and heated to 80° C. for 10 min to halt the reaction. Resultant cDNA was stored at −20° C.

The preparation of primers and mutated internal standards was as follows: primers were made using an Applied Biosystems Model 391 PCR-Mate DNA Synthesizer. Ideal sequences were obtained by using the Oligo-TM Primer Analysis Software (National Biosciences, Hamel, Minn.). The primer sequences are described below.

Glutathione Peroxidase (GSH-Px) (Chada et al., *Genomics* 6:268–271, 1990)

The "outer" primers used to amplify both the native and mutated templates result in a product length of 354 base pairs. The "outer" primers are (Seq. ID No. 1) Pos. 241 5'-GGGCCTGGTGGTGCTTCGGCT-3' (coding sense) correspond to bases 241–261 of the cloned sequence, and (Seq. ID No. 2) Pos. 574 5'-CAATGGTCTGGAAGCGGCGGC-3' (anti-coding sense) which anneals to bases 574–594.

The "inner" primers used to synthesize the mutated internal standard remove an EcoRI restriction endonuclease recognition site (GAATTC) by changing a native cDNA base pair (bold bases). The "inner" primers are (Seq. ID No. 3) Pos. 309 5'-ATTCT GATTTC CCTCAAGTACGTCCGGCCT-3' (coding sense)

(Seq. ID No. 4) Pos. 309 3'-TAAGA CTAAAG GGAGTTCATGCAGGCCGGA-5' (anti-coding sense)

Both primers correspond to bases 309–338 of the cloned sequence. The mutation results from the substitution of a T for the native A at position 316 of the sense strand. Restriction endonuclease digestion of the native GSH-Px yields products of 280 and 74 base pairs.

Glyceraldehyde-3-Phosphate Dehydrogenase (GAPDH) (Tso et al., *Nucleic Acids Res.* 13:2485–2502, 1985)

The "outer" primers used to amplify both the native and mutated templates result in a product length of 788 or 790 base pairs. The "outer" primers are:

(Seq. ID No. 5) Pos. 46 5'-GGTCGGAGTCAACGGATTTGGTCG-3' (coding sense) corresponding to bases 9–32 of the cloned sequence, and (Seq. ID No. 6) Pos. 812 5'-CCTCCGACGCCTGCTTCACCAC-3' (anti-coding sense) which anneals bases 777–798.

The "inner" primers used to synthesize the mutated template create an EcoRI restriction endonuclease recognition site (GAATTC) by changing one native cDNA base pair (bold bases). The "inner" primers are:

(Seq. ID No. 7) Pos. 234 5'-TGATCAATG GAATTC CCATCACCA-3' (coding sense)

(Seq. ID No. 8) Pos. 234 3'-ACTAGTTAC CTTAAG GGTAGTGGT-5' (anti-coding sense)

Both primers correspond to bases 199–222 of the cloned sequence. The mutation results from the substitution of a T for the native A at position 211 of the sense strand. Restriction endonuclease digestion of the mutated GAPDH yields products of 588 and 200 base pairs.

Several studies were performed using a different mutated GAPDH template. This template had a novel BamHI restriction site introduced.

The "outer" primers used to amplify both the native and mutated templates result in a product length of 634 base pairs. The "outer" primers are:

(Seq. ID No. 9) Pos. 200 5'-CATGGCACCGTCAAGGCTGAGAAC-3' (coding sense) corresponding to bases 165–188 of the cloned sequences, and (Seq. ID No. 10) Pos. 813 5'-CCTCCGACGCCTGCTTCACCAC-3' (anti-coding sense) which anneals to bases 777–798.

The "inner" primers used to synthesize the mutated template create a BamHI restriction endonuclease recognition site (GGATCC) by changing one native cDNA base pair (bold bases). The "inner" primers are:

(Seq. ID No. 11) Pos. 368 5'-CAGGGG GGATCC AAAAGGGTCATCAT-3' (coding sense)

(Seq. ID No. 12) Pos. 368 3'-GTCCCC CCTAGG TTTTCCCAGTAGTA-5' (anti-coding sense)

Both primers correspond to bases 333–358 of the cloned sequence. The mutation results from the substitution of a T for the native G at position 342 of the sense strand. Restriction endonuclease digestion of this mutated GAPDH yields products of 460 base pairs and 174 base pairs.

The mutated internal standards were prepared by site directed mutagenesis as described by Higuchi et al., *Nucleic Acids Res.* 16:7351–7367, 1988. These single base mutations resulted in either the gain (GAPDH) or loss (PSH-Px) of an EcoRI restriction endonuclease recognition site. (Several studies used a muted GAPDH with a BamHI site introduced). Briefly, for each mutated product, 2 initial PCR reactions using an "outer" primer and an "inner" single base mismatched primer produced two overlapping DNA fragments. (Primers 1 and 4, 2 and 3 for GSH-Px; Primers 5 and 8, 6 and 7 for GAPDH). These overlapping DNA fragments were electrophoresed on a 3% Nusieve, 1% LE agarose ethidium bromide stained gel. Bands were excised and purified using Millipore Ultrafree-MC 0.45 μM filter (Nihon Millipore Kogyo K.K., Yonezawa, Japan). The purified DNA was ethanol precipitated, washed, vacuum dried and taken up in 100 μL sterile dH20. 1 μL of each of the two overlapping DNA fragments were PCR amplified using the outer primers only. The first PCR cycle was performed without primers to allow for heterodimer formation. The entire mutated product was thus formed and amplified. The mutated PCR product was gel purified as described above and reamplified to form bulk product. The bulk product was gel purified and measured spectrophotometrically. The mutated products were diluted to the attomolar range for use as competitive templates. Herring sperm DNA (Lofstrand, Bethesda, Md.) 1 μg/ml was used as a carrier. Restriction endonuclease digestion was performed on samples of each mutated template to assure lack of contamination.

The PCR conditions were as follows: The PCR conditions were standardized for each experiment by using a master mixture containing 1×PCR buffer (50.0 mM KCl, 10.0 mM Tris-HCl pH 9.0, 1.5 mM $MgCl_2$), 25 pmoles of primers coding for GSH-Px and GAPDH, 0.2 mM dNTP's (A,T,C, G), and constant amounts of both internal standards per 100 μL reaction mixture. Taq DNA polymerase (2.5 units) was added to each 100 μL reaction prior to amplification. cDNA obtained from the BEP2D cell line was serially diluted and added to the sample PCR tubes. In all experiments, control tubes containing no template, native cDNA only, or mutated standards only were amplified to check for contamination or complete enzyme digestion.

PCR amplification was carried out for 35 cycles at 94° C. for one min, 60° C. for one min, and 72° C. for one min. After amplification, PCR products were heated for 10 min in order to maximize heterodimer formation.

The quantification of products was as follows: Samples (40 μL) for each PCR tube were EcoRI restriction endonuclease digested for 12–16 hours (Studies done using mutated GAPDH with the novel BamHI restriction site were also BamHI restriction endonuclease digested for 4–5 hours). These products were electrophoresed on a 3% Nusieve, 1% LE agarose ethidium bromide stained gel for 2–3 hours at 60 V. A negative photograph was taken of the gel using Polaroid 665 positive/negative instant film The negative photograph was subjected to densitometry (Zeineh Soft Laser Scanning Densitometer Model SLR 2D/1D using Zeineh 1D Autostepover Videophoresis Program Software, Biomed Instruments, Fullerton, Calif.). Areas under each curve were calculated and used for quantification. Corrections were made for relative band sizes and heterodimer formation. Data were expressed GSH-Px to GAPDH relative ratios.

RESULTS

Figure 1:
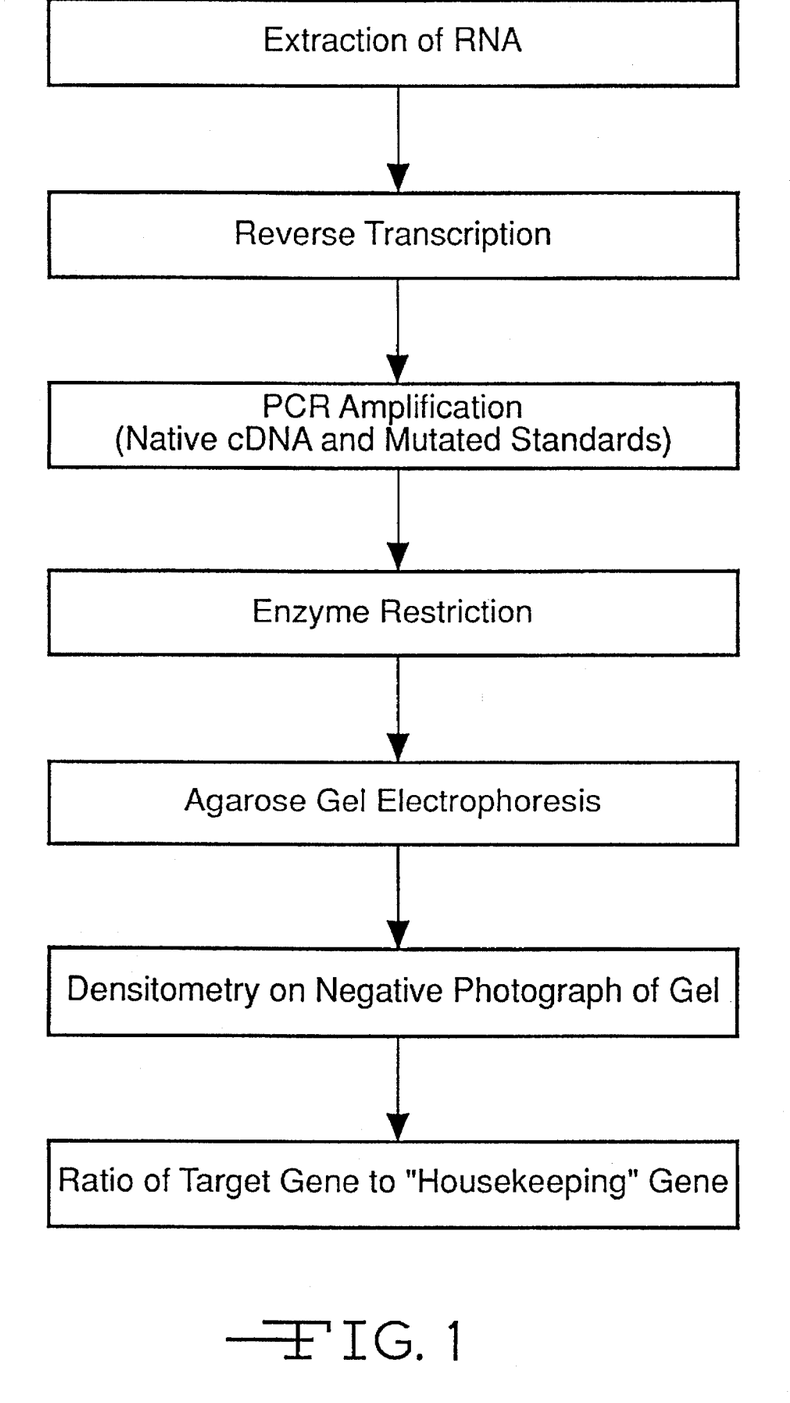
FIG. 1 is a schematic diagram of the work scheme for PCR quantification of relative target gene expression.
Figure 2:
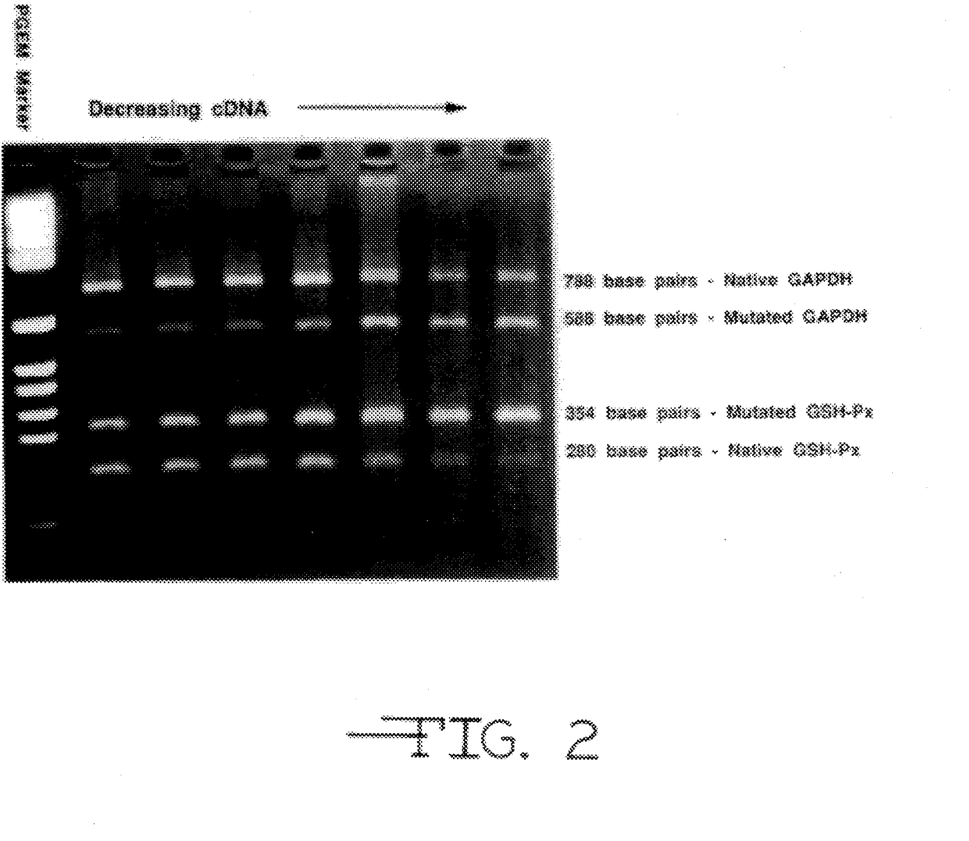
FIG. 2 is a photograph showing serial dilutions of BEP2D cDNA (representing 0.25 µg to 0.05 µg total RNA) were co-amplified with constant amounts of each single base mutated internal standard (10 attamoles each), subjected to EcoRI restriction endonuclease digestion and electrophoresed on an agarose gel as described in the methods section. A negative photograph of this gel was then subjected to densitometry in order to quantify bands.

The procedure used for PCR quantitation is shown schematically in FIG. 1. Serial dilutions of BEP2D cDNA (representing 0.25 μg to 0.05 μg total RNA) were co-amplified with constant amounts of each single base mutated internal standard (10 attamoles each), then analyzed as described above. A negative photograph of the gel was analyzed by densitometry in order to quantify each band, as seen in FIG. 2.

Using the area under each curve, relative ratios between native/mutated products were obtained. Corrections were made for relative band sizes (i.e. mutated GAPDH was multiplied by 788/588 when compared to native GAPDH and native GSH-Px was multiplied by 354/280 when compared to mutated GSH-Px). Heterodimer formation was maximized following PCR by heating the products to 100° C. for 10 min followed by slow cooling. Following maximization of heterodimers, the quantity of each product was determined by analysis of the densitometric data using the quadratic formula as the formation of heteroduplexes follows a binomial distribution under these conditions (Gilliland et al, *Proc. Natl. Acad. Sci.* 87:2725–2729 (1990), Becker-Andre et al., *Nucleic Acids Res.* 17:9437–9446 1989). Final values were expressed as an odds ratio of GSH-Px native/mutated to GAPDH native/mutated. While the graph, shown in FIG. 3, of the amount of native product (in arbitrary densitometric units) vs. total starting RNA did not remain linear throughout the either GSH-Px or GAPDH, the graph of the ratios of GSH-Px native/mutated vs. total starting RNA and GAPDH native/mutated vs. total starting RNA was linear for both genes. By averaging the ratio obtained from each sample tube (2.18:1, 1.14:1, 2.00:1, 1.76:1, 2.46:1, 2.71:1, and 1.92:1), we obtained a mean value of the ratio GSH-Px native/mutated to GAPDH native/mutated of 2.17:1 with a S.D. of 0.33. No value varied more than 25% from the mean.

To assess the variability of this technique, a repeat of the above experiment was performed using new dilutions of mutated standards and master mixture. By averaging the ratio obtained from each sample tube (1:9.09, 1:8.13, 1:9.43, 1:8.13, 1:6.62, 1:8.77, 1:7.69, 1:10.00, 1:7.58, and 1:7.04), a mean value of the ratio of GSH-Px native/mutated to GAPDH native/mutated of 1:8.25 with a S.D. of 1.07 was obtained. No value varied more than 22% from the mean. This confirms the precision of this technique and also illustrates the variability introduced by new master mixtures containing new dilutions of mutated standards.

To assess the variability between samples using the same master mixture and dilutions of mutated standards, BEP2D RNA was independently extracted from three separate flasks and reverse transcribed to cDNA. Only coarse (5 fold) dilutions of cDNA were performed. Four PCR tubes were run for each study. The obtained ratios of GSH-Px native/mutated to GAPDH native/mutated were 15.01:, 17.69:1, and 21.76:1 (mean=18.15, S.D.=3.40). All 3 values were within 20% of the mean. This confirms the precision of this technique when comparing samples that have been independently reverse transcribed but amplified with the same master mixture and internal standard dilutions.

Northern analysis of BEP2D RNA performed in our laboratory reveals a ratio of GSHPx/GAPDH mRNA of approximately 1:8. (Data not shown).

---

What is claimed:

1. Method for quantitative measurement of expression of a target gene comprising:
   a) isolating at least a portion of a RNA sequence which encodes the RNA for the target gene and a portion of an RNA for a housekeeping gene, which RNA has been isolated from a sample cell;
   b) subjecting the RNA sequence of step a) and two internal mutated standards comprising single base routants of the target gene and the housekeeping gene cDNA that cause either a loss or gain of an EcoRI restriction endonuclease recognition site to reverse transcription to obtain at least one native cDNA which encodes the DNA for both the target gene and at least one native cDNA which encodes the DNA for the housekeeping gene;
   c) conducting polymerase chain reaction amplification of the native cDNA in the presence of target gene and housekeeping gene primers and a predetermined quantified amount of the routate internal standards;
   d) conducting a quantification step of products of the polymerase chain reaction amplification of step c) by
      i) maximizing heterodimer formation,
      ii) calculating the quantities of the products, and
      iii) comparing samples of the products simultaneously using a master mixture which is the same for each product and having the same dilution of internal standards;
   e) subjecting the amplified cDNA of step c) to enzyme restriction by digesting with EcoRI;
   f) subjecting the digested cDNA of step e) to electrophoresis to separate wild type from mutated products; and
   f) measuring the expression of the target gene relative to the housekeeping gene to provide the quantitative measurement of expression of the target gene.

2. The method of claim 1, wherein the housekeeping primer comprises at least one oligonucleotide homologous to the cDNA of a housekeeping gene selected from the group comprising GAPDH, β-actin, 28S RNA and 18S RNA genes and containing known restriction endonuclease recognition site sequences or one or two base pair mismatches for restriction endonuclease recognition sequences.

3. The method of claim 1, wherein the housekeeping primer comprises at least two oligonucleotides that contain sequences homologous to sequences in the housekeeping genes, which housekeeping primer sequences are useful for generating artificially shortened competitive templates.

4. The method of claim 1, in which the quantification step is conducted at a non-exponential phase of the polymerase chain reaction amplification.

5. The method of claim 1, in which the quantification step comprises calculating the quantities of the products as an odds ratio of native target gene/mutated target gene to native housekeeping gene/mutated housekeeping gene.

6. The method of claim 1, in which the master mixture comprises approximately 1×PCR buffer (50.0 mM KCl, 10.0 mM Tris-HCl, 1.5 mM $MgCl_2$), 25 pmoles of primers coding for the target gene and the housekeeping gene, 0.2 mM dNTP's (A,T,C,G) and constant amounts of both internal standards per 100 µL reaction mixture.

7. A method for quantitative measurement of gene expression of a target gene comprising:
  a) isolating cellular mRNA of a target gene and a housekeeping gene which are reverse transcribed and specifically amplified in the presence of competitive template such that a ratio of the target gene to the housekeeping gene is obtained and that ratio is used to assess the amount of gene expression of the target gene by conducting simultaneous polymerase chain reaction amplification of a mixture of the following:
    i) at least one oligonucleotide primer pair of at least one target gene,
    ii) at least one oligonucleotide primer pair of at least one housekeeping gene,
    iii) at least one mutated competitive template of the target gene,
    iv) at least one mutated competitive template of the housekeeping gene, and
    v) native cDNA which contains at least one copy of the target gene cDNA and at least one copy of the housekeeping gene cDNA; to form polymerase chain reaction cDNA products comprising: native cDNA of the target gene and the housekeeping gene, and mutated cDNA of the target gene and the housekeeping gene;
  (b) isolating the cDNA products; and,
  (c) detecting the relative presence of the native cDNA products and mutated cDNA products by comparing the amount of native cDNA coding for the target gene and the amount of mutated cDNA coding for the competitive template of the target gene to the amount of native cDNA coding for the housekeeping gene and the amount of mutated cDNA coding for the competitive template of the housekeeping gene; wherein comparison of the relative presence of the amounts of native cDNA products and mutated cDNA products of the target gene and the housekeeping gene provide the quantitative measurement of the expression of the target gene.

8. The method of claim 7, in which the mutated competitive templates of the target gene and of the housekeeping gene: a) comprise at least one oligonucleotide that contains a sequence homologous to the target gene or the housekeeping gene, respectively; and b) contain at least one known restriction endonuclease recognition site sequence or a point mutation for the restriction endonuclease recognition sequence.

9. The method of claim 8 in which the point mutation comprises one or two base pair mismatch.

10. The method of claim 9 in which the point mutation causes either a gain or a loss of an EcoRI restriction endonuclease recognition site.

11. The method of claim 7 in which the target gene and the housekeeping gene have the same recognition site.

12. The method of claim 7 in which the cDNA products are isolated by subjecting the cDNA products to digestion with a restriction enzyme, and thereafter subjecting the digested cDNA products to electrophoresis to separate the native cDNA products from the mutated cDNA products.

13. The method of claim 12 in which the mutated competitive template of the target gene causes a loss of an EcoRI restriction site and the mutated competitive template of the housekeeping gene causes a gain of an EcoRI restriction site.

14. The method of claim 13 in which the cDNA products are digested with EcoRI.

15. The method of claim 7 in which the mutated competitive templates of the target gene and the housekeeping gene comprise artificially shortened competitive templates.

16. The method of claim 7 in which the polymerase chain reaction amplification is allowed to proceed to a point which maximizes heterodimer formation.

17. The method of claim 7 in which at least one housekeeping gene is selected from the group comprising glyceraldehyde phosphate dehydrogenase (GAPDH), β-actin or 28S RNA.

18. The method of claim 7 in which the mutated internal standard competitive templates are prepared by site directed mutagenesis.

19. The method of claim 7 in which prior to the simultaneous polymerase chain reaction amplification for each mutated competitive template:
  i) two initial polymerase chain reactions are conducted using an outer primer and an inner single base mismatched mutated internal standard competitive template primer to produce two overlapping DNA fragments;
  ii) isolating and purifying the overlapping DNA fragments of the initial polymerase chain reaction of step (i) above;
  iii) polymerase chain reaction amplifying each of the two overlapping DNA fragments using the outer primers only;
  iv) conducting a polymerase chain reaction amplification according to claim 7 above without the primers to allow for heterodimer formation; and,
  v) purifying and amplifying the polymerase chain reaction products of step (iv) above and thereafter diluting to use as competitive templates.

20. A method for quantitative measurement of gene expression of a target gene in tissue samples comprising:
  a) synthesizing at least one oligonucleotide primer pair of at lest one housekeeping gene,
  b) synthesizing at least one oligonucleotide primer pair of at least one target gene,
  c) synthesizing at least one competitive template of the housekeeping gene,
  d) synthesizing at least one competitive template of the target gene,
  e) isolating at least a portion of an RNA sequence from said tissue samples,
  subjecting the RNA sequence to reverse transcription to obtain at least one native cDNA, g) conducting polymerase chain reaction amplification of the native cDNA in the presence of the target gene oligonucleotide primers, the housekeeping gene oligonucleotide primers, and predetermined quantities of the housekeeping gene competitive template and the target gene competitive template, h) subjecting amplified cDNA products of step "g" above to digestion with at least one restriction enzyme, i) subjecting the digested cDNA to electrophoresis to separate the amplified target gene and the amplified housekeeping gene from the amplified target gene competitive template and the amplified housekeeping gene competitive template, and j) measuring the relative expression of the target gene in at least one tissue sample by dividing a ratio of the target gene to a known amount of the competitive template of the target gene by a ratio of housekeeping gene to a known amount of the competitive template of the housekeeping gene to provide the quantitative measurement of expression of the target gene.

21. The method of claim 20 which further comprises making artificially shortened competitive templates of the housekeeping gene to serve as an internal mutated standard competitive template of the housekeeping gene such that there is no need for subjecting the amplified cDNA to restriction enzyme digestion.

22. The method of claim 20 in which polymerase chain reaction products are denatured at about 94° C. An slowly cooled to allow heterodimer formation.

* * * * *